(12) United States Patent
Virshup et al.

(10) Patent No.: US 9,620,256 B2
(45) Date of Patent: Apr. 11, 2017

(54) X-RAY IMAGING DEVICE INCLUDING ANTI-SCATTER GRID

(71) Applicants: Varian Medical Systems, Inc., Palo Alto, CA (US); Varian Medical Systems International AG, CH-6303 Zug (CH)

(72) Inventors: Gary Virshup, Cupertino, CA (US); Heinrich Riem, Baden-Daettwil (CH)

(73) Assignees: Varian Medical Systems, Inc., Palo Alto, CA (US); Varian Medical Systems International AG, Zug (DE)

( * ) Notice: Subject to any disclaimer, the term of this patent is extended or adjusted under 35 U.S.C. 154(b) by 37 days.

(21) Appl. No.: 14/474,684

(22) Filed: Sep. 2, 2014

(65) Prior Publication Data

US 2015/0085990 A1 Mar. 26, 2015

Related U.S. Application Data

(60) Provisional application No. 61/882,846, filed on Sep. 26, 2013.

(51) Int. Cl.
*A61B 6/00* (2006.01)
*G21K 1/02* (2006.01)
*G01T 1/20* (2006.01)

(52) U.S. Cl.
CPC ............ *G21K 1/025* (2013.01); *A61B 6/4233* (2013.01); *A61B 6/4283* (2013.01); *A61B 6/4291* (2013.01); *G01T 1/20* (2013.01)

(58) Field of Classification Search
CPC ... A61B 6/4233; A61B 6/4283; A61B 6/4291; G03B 42/04
See application file for complete search history.

(56) References Cited

U.S. PATENT DOCUMENTS

| | | | | |
|---|---|---|---|---|
| 5,844,961 A * | 12/1998 | McEvoy | .............. | A61B 6/4494 348/E5.086 |
| 6,064,720 A * | 5/2000 | Piscitelli | .................. | A61B 6/00 378/154 |
| 6,967,333 B2 * | 11/2005 | Hata | ..................... | G01T 1/1648 250/370.09 |
| 7,435,967 B2 * | 10/2008 | Ertel | ..................... | G01T 1/1644 250/370.09 |
| 7,569,831 B2 * | 8/2009 | Jadrich | ................. | G01T 1/2928 250/370.11 |
| 7,742,561 B2 * | 6/2010 | Ueki | .................... | A61B 5/0091 378/37 |
| 8,331,536 B2 * | 12/2012 | Shaw | ....................... | A61B 6/06 378/154 |
| 2004/0234036 A1 * | 11/2004 | Klausz | .................. | G03B 42/02 378/154 |
| 2004/0251438 A1 * | 12/2004 | Iwakiri | ................ | G03G 15/045 250/591 |
| 2008/0279330 A1 * | 11/2008 | Ueki | .................... | A61B 5/0091 378/63 |
| 2010/0148081 A1 * | 6/2010 | Yoshimi | .................. | A61B 6/00 250/370.08 |
| 2010/0187427 A1 * | 7/2010 | Kuwabara | ................ | A61B 6/56 250/370.08 |

(Continued)

*Primary Examiner* — Thomas R Artman
(74) *Attorney, Agent, or Firm* — Houst Consulting

(57) ABSTRACT

An x-ray imaging device includes an anti-scatter grid placed inside the housing of the imaging device and adjacent to an x-ray detector.

8 Claims, 2 Drawing Sheets

(56) References Cited

U.S. PATENT DOCUMENTS

| | | | | |
|---|---|---|---|---|
| 2011/0069816 A1* | 3/2011 | Shaw | ............... | A61B 6/06 378/154 |
| 2012/0318991 A1* | 12/2012 | Ohta | ............... | A61B 6/00 250/366 |
| 2015/0085990 A1* | 3/2015 | Virshup | ............ | G01T 1/20 378/154 |

* cited by examiner

X-RAY IMAGING DEVICE INCLUDING ANTI-SCATTER GRID

CROSS REFERENCE TO RELATED APPLICATIONS

This application claims priority to and benefit of U.S. Provisional Application 61/882,846 filed on Sep. 26, 2013 under 35 U.S.C. §119(e), the disclosure of which is incorporated herein by reference.

TECHNICAL FIELD

Embodiments of this disclosure relate to x-ray imaging devices and methods. In particular, x-ray imaging devices including an anti-scatter grid are described.

BACKGROUND

Anti-scatter grids are known and have been used on x-ray imagers to reduce the effects of scatter. Conventionally, anti-scatter grids are attached to the outside of the device housing. The grid lines are visible on an image and the x-ray shadow of their typically lead lamella can be calibrated out of the image. For applications where the imager and/or the x-ray source are moved relative to each other, there is the possibility that the imager will no longer be pointing in the same direction towards the x-ray source during imaging as was done during calibration. As such, the shadow of the lamella can fall on different pixels thus causing regular lines in the digital image. While these lines may be corrected by computer software, it would be desirable to not generate them in the first place. Further, computational corrections may reduce resolution, create unwanted new artifacts, and increase the time before images are ready for viewing or other operations such as cone beam reconstruction. The added complexity of the corrections may also add costs to system development.

In some conventional devices, the anti-scatter grids are movable in response to the motion of the detector by using a fixture on the outside of device housing. However, movable grids may increase sensitivity to pointing accuracy as the grids move further from the imaging plane.

SUMMARY

This disclosure provides an x-ray imaging device that includes an anti-scatter grid integral to the inside of the device. The disclosed imaging device allows an anti-scatter grid to be placed as close to a detector as possible to reduce the effect of pointing error.

An anti-scatter grid may be placed above a detector and below the housing of an imaging device. The grid may be attached to the housing via an attachment member, which can hold the grid in position as the imaging device is moved in use. For example, holes and other suitable means may be provided in the periphery of the anti-scatter grid to allow attachment of the grid to the housing. In some embodiments, for example where there are minimal forces on the imaging device when in use, attachment parts may not be needed and/or be replaced with an adequate compression.

Therefore, alternative or in addition to an attachment member, a compressible body such as compression foam may be placed above and below the anti-scatter grid. For example, a slit may be provided in a compression form so that the anti-scatter grid can be received and held in place. As such, the anti-scatter grid may be sandwiched between two pieces of compression foam, e.g., a thinner piece below the grid and a thicker piece above the grid. This may be desirable in situations where an anti-scatter grid is designed non-compressible and compression may be needed to hold a detector in place. In some embodiments, compression foam may not be required and the anti-scatter grid can be free standing inside the housing of the imaging device.

This summary is provided to introduce selected embodiments in a simplified form and is not intended to identify key features or essential characteristics of the claimed subject matter, nor is it intended to be used as an aid in determining the scope of the claimed subject matter. Other embodiments are described in the Detail Description.

BRIEF DESCRIPTION OF THE DRAWINGS

These and other features and advantages of the disclosed methods and apparatuses will become better understood upon reading of the following detailed description in conjunction with the accompanying drawings and the appended claims provided below, where:

DETAILED DESCRIPTION

Figure 1:
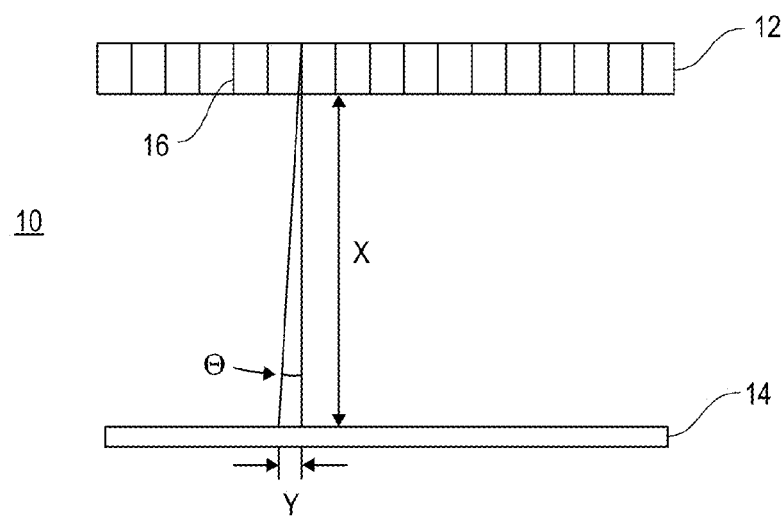
FIG. 1 schematically illustrates a general geometry of an anti-scatter grid relative to a detector in an imaging device.

Various embodiments of an x-ray imaging device and an imaging method are described. It is to be understood that the disclosure is not limited to the particular embodiments described as such may, of course, vary. An aspect described in conjunction with a particular embodiment is not necessarily limited to that embodiment and can be practiced in any other embodiments. Further, in the following description, specific details such as examples of specific materials, dimensions, processes, etc. may be set forth in order to provide a thorough understanding of the disclosure. It will be apparent, however, to one of ordinary skill in the art that these specific details need not be employed to practice embodiments of the disclosure. In other instances, well known components or process steps may not be described in detail in order to avoid unnecessarily obscuring the embodiments of the disclosure.

Various relative terms such as "top," and "bottom," "upper," "lower," "above," "under," "front," "back," etc. may be used to facilitate description of various embodiments. The relative terms are defined with respect to a conventional orientation of a structure and do not necessarily represent an actual orientation of the structure in manufacture or use. The following detailed description is, therefore, not to be taken in a limiting sense. As used in the description and appended claims, the singular forms of "a," "an," and "the" include plural references unless the context clearly dictates otherwise.

As used herein, the term "x-ray detector" refers to an assembly which includes an x-ray conversion layer such as a scintillator or photoconductor layer configured to convert x-ray photons to visible light or electron-hole charges and a detector array configured to detect the generated visible light or electron-hole charges. An x-ray detector may also include a base plate or substrate on which the detector array and/or the x-ray conversion layer are formed. As used herein, the term "digital x-ray detector" refers to an x-ray detector which comprises electrical circuits configured to access and read electrical signals and convert analog signals to digital data for further processing.

By way of example, a scintillator-based digital x-ray detector may include a large number of e.g. hundreds of thousands or millions of detection pixels arranged in rows and columns or other patterns forming an active detection area. Each detection pixel may include a photosensitive element for detecting light and producing electrical charges and a switching element for allowing access to the electrical charges. The photosensitive element may be a photodiode, a photogate, phototransistors, or other photosensitive elements. The switching element may be a thin-film transistor (TFT) such as amorphous silicon (a-Si) TFT or other switching elements such as organic transistors, charge coupled devices (CODs), CMOS, metal oxide transistors, or transistors made of other semiconductor materials, and/or switching diodes. Optionally, a detection pixel may contain other components for signal or charge buffering and amplification. The electrical signals in the detection pixels may be accessed by drive circuits and read by readout circuits. The electrical signals may be converted by analog-to digital converters (ADCs) and the resulting digitized signal data can be then processed and/or displayed. Other electrical circuits may be included to perform such as buffering, amplification, multiplexing etc.

Similarly, a photoconductor-based digital x-ray detector may include a large number of e.g. hundreds of thousands or millions of detection pixels arranged in rows and columns or other patterns forming an active detection area. Unlike a scintillator-based digital x-ray detector whose detection pixels include photosensitive elements to produce electrical signals from light generated by a scintillator layer, a photoconductor-based digital x-ray detector employs a photoconductor layer to generate electron and hole charges directly from x-ray photons. The electron and hole charges may be collected by charge-collection electrodes in the detection pixels. The collected charges may be accessed, read, digitized using electrical circuits similar to those in a scintillator-based digital detector.

As used herein, the term "scintillator layer" refers to a functional layer in an x-ray detector which is configured to generate visible light from x-ray photons. The generated visible light may be detected by photosensitive elements in the x-ray detector, which may produce electrical charges proportional to the intensity of the visible light. Suitable scintillator materials include and are not limited to gadolinium oxisulfide ($Gd_2O_2S:Tb$), cadmium tungstate ($CdWO_4$), bismuth germanate ($Bi_4Ge_3O_{12}$ or BGO), cesium iodide (CsI), cesium iodide thallium (CsI:Tl), or any combination thereof. The scintillator may be structured or pixilated. A structured scintillator may include columnar or needle-like structures, which may act as light pipes channeling light emitted within them toward detection pixels. A pixilated scintillator matrix may be formed by slicing the scintillator crystal into parallelepipeds, which are then coated with a layer of reflective or absorptive coating and joined back together. A structured or pixilated scintillator may reduce light spread in the scintillator and help improve resolution. Alternatively, the scintillator layer can be non-structured or non-pixilated. Use of a clear or continuous scintillator may reduce the cost of making imaging devices.

As used herein, the term "photoconductor layer" refers to a functional layer in an x-ray detector which is configured to generate electron-hole pairs from x-ray photons. The generated electrons and holes may be collected by an array of charge-collection electrodes and detected by a detector array. Suitable photoconductor material include and are not limited to mercuric iodide ($HgI_2$), lead iodide ($PbI_2$), bismuth iodide ($BiI_3$), cadmium zinc telluride (CdZnTe), amorphous selenium (a-Se), etc.

As used herein, the term "anti-scatter grid" refers to a device configured to reduce the level of scattered radiation received by an x-ray detector. Radiation scattering occurs when incident x-ray photons interact with the object being imaged. Scattered radiations pass through the object with an angle significantly deviating from its original incident path and are of no diagnostic value since the recorded signals do not relate to the anatomy of the object or patient. Scattered radiations cause artifacts and reduce contrast in images. An anti-scatter grid may include a series of lamellas or strips of radiation absorbent material (grid material), alternating with sections of radiolucent material (inter-space material). An anti-scatter grid may be designed to transmit those radiations whose directions are on straight lines from the radiation source to the detection elements of an x-ray detector. Scattered radiations that travel obliquely are generally absorbed in the grid material.

Suitable grid materials include dense elements or alloys having a high atomic number such as e.g. lead, tungsten, tantalum, uranium, thorium, iridium, gold, and their alloys etc. Suitable interspace materials include elements or composites with a low atomic number such as e.g. aluminum, beryllium, plastics such as methacrylate plastics, carbon fiber composites, solid foams of various materials, or aerogels etc. The grid ratio (the height of the grid strip divided by the thickness of the interspace material), grid frequency (the number of grid strips per inch or centimeter), and other grid parameters can be optimized to enhance the performance of the grid. The anti-scatter grid as used herein may be a focused grid. A focused grid has a geometric pattern in which the grid members or strips are arranged generally parallel to the radiation beams emanating from the focal spot of the source. For example, the grid strips may be aligned so that if they were extended, the grid strips would intersect along an imaginary convergence line.

As used herein, the term "compressible body" refers to a body capable of being compressed by a compression force inserted by a device housing member such as a housing cover plate against an x-ray detector contained inside of the housing member. The compression of a compressible body may transmit a force to an x-ray detector below the compressible body, thereby holding the x-ray detector in place. Materials suitable for a compressible body include and are not limited compression foam, such as polyester foam, polyurethane foam, silicone foam, and thermoplastic elastomer foam, etc.

As used herein, the term "distance between an anti-scatter grid and an x-ray detector" refers to the distance between the side of the anti-scatter grid that is proximal to the x-ray detector and the side of the x-ray detector that is proximal to the grid.

An x-ray imaging device is provided in this disclosure. The x-ray imaging device includes a housing, an x-ray detector placed inside the housing, and an anti-scatter grid placed inside the housing adjacent to the x-ray detector.

The x-ray imaging device may include a compressible body between a cover plate of the housing and the x-ray detector. The compressible body may be compression foam. The compressible foam may be compressed by a compression force inserted by the housing cover plate. The compression of the compressible foam may transmit a force to the anti-scatter grid and/or x-ray detector below the compressible foam, thereby holding the grid and/or detector in place.

The compression foam may include a first piece and a second piece, and the anti-scatter grid may be sandwiched between the first and second pieces. The first piece of the compression foam may be in between the housing cover plate and the anti-scatter grid, and the second piece of the compression foam may be in between the anti-scatter grid and the x-ray detector. The second piece of the compression foam may be thinner than the first piece of the foam to allow the grid to be placed close to the detector.

Alternative or in addition to the compressible body, the anti-scatter grid may be attached to the housing by an attachment member.

The x-ray detector of the imaging device may be a digital flat panel detector comprising a scintillator layer configured to convert x-ray photons to visible light. The x-ray detector of the imaging device may also be a digital flat panel detector comprising a photoconductor layer configured to convert x-ray photons to electron-hole charges.

The anti-scatter grid may be distanced from the x-ray detector about 1-15 mm, or about 3-5 mm. The anti-scatter grid may also be placed directly on the x-ray detector.

Exemplary embodiments will now be described with reference to the figures. It should be noted that some figures are not necessarily drawn to scale. The figures are only intended to facilitate the description of specific embodiments, and are not intended as an exhaustive description or as a limitation on the scope of the disclosure.

FIG. 1 is a diagram schematically illustrating a general geometry of an anti-scatter grid 12 relative to an x-ray detector 14. In FIG. 1, the distance between the grid 12 and the x-ray detector 14 is represented by X. The misalignment angle of a grid lamella 16 relative to the x-ray detector 14 (pointing inaccuracy) is represented by Θ. The grid lamella shadow shift caused by pointing inaccuracy is represented by Y. The relationship between the variables X, Y, and Θ can be described by the following trigonometric equations:

$$Y = X * \mathrm{Tan}(\Theta) \quad \text{(I)}$$

$$\Theta = \mathrm{Tan}{-1}(Y/X) \quad \text{(II)}$$

Equations (I) and (II) indicate that by placing the anti-scatter grid 12 closer to the detector 14 (variable X), the grid lamella shadow shift (variable Y) can be reduced for the same pointing inaccuracy (Θ). Alternatively, Equations (I) and (II) show that reducing the spacing between the anti-scatter grid 12 and the detector 14 (variable X) may allow a greater misalignment tolerance or pointing inaccuracy (Θ) between the grid 12 and the detector 14 for the same lamella shadow shift (Y).

Figure 2:
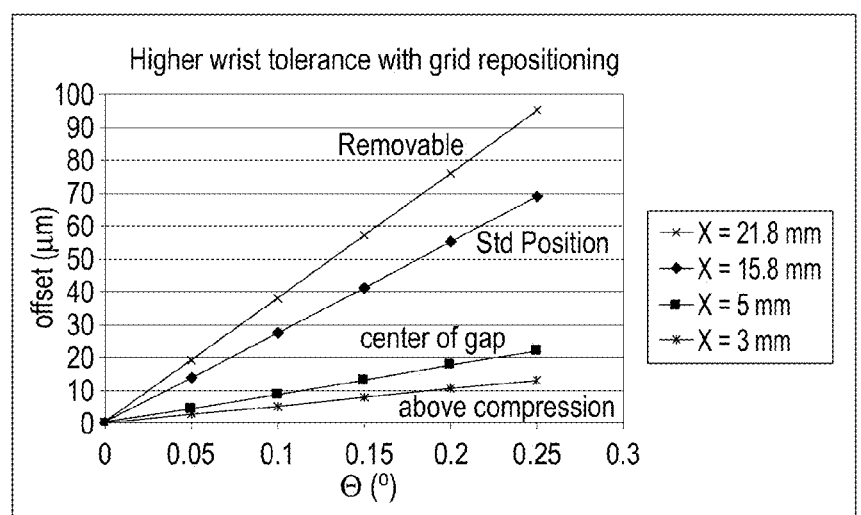
FIG. 2 is a graph showing the major pointing tolerance to the spacing between the anti-scatter grid and the detector.

FIG. 2 is a graph showing the major pointing tolerance with the spacing between the anti-scatter grid 12 and the detector 14. In FIG. 2, the horizontal axis represents the pointing tolerance or inaccuracy (Θ) of the grid 12 and the vertical axis represents the grid lamella shadow shift or offset. As shown in FIG. 2, the grid lamella shadow shift can be reduced by a factor of about 5.2 when the spacing between the anti-scatter grid 12 and the detector 14 is reduced from 15.8 mm to 3 mm. In conventional x-ray imaging devices, an anti-scatter grid is typically attached to the outside of the housing cover plate of the imaging device and the spacing between the anti-scatter grid and the detector is about 15.8 mm. If a removable grid holder is used as in conventional x-ray imaging devices, the spacing between the anti-scatter grid and the detector could be about 21.8 mm or greater.

Another way to look at the improvement by reducing the spacing between the anti-scatter grid and the detector is that a 0.25° grid lamella misalignment with 3 mm spacing is an equivalent to a 0.05° misalignment with 15.8 mm spacing. In other words, the pointing tolerance is increased by about 5 times.

Figure 3:
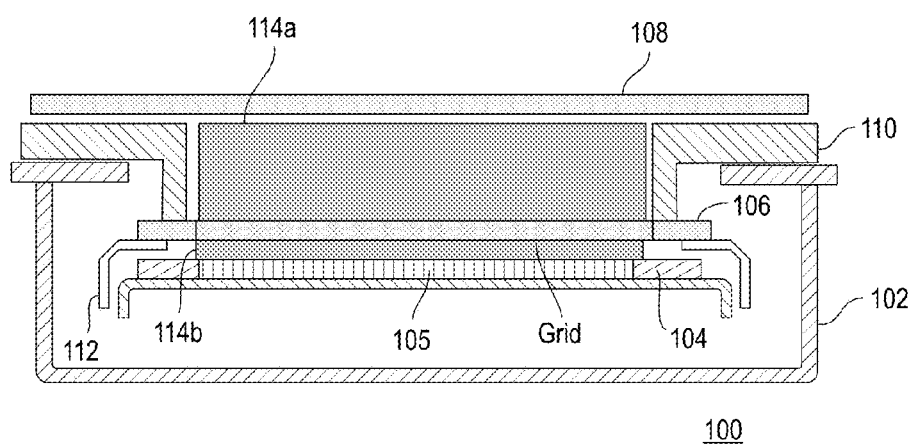
FIG. 3 schematically illustrates an exemplary x-ray imaging device including an anti-scatter grid according to some embodiments of the disclosure.

FIG. 3 schematically illustrates an exemplary x-ray imaging device 100 according to some embodiments of the disclosure. As shown, the x-ray imaging device 100 may include a housing 102 and a detector 104 placed inside of the housing 102. An anti-scatter grid 106 may be placed inside of the housing 102 and adjacent to the detector 104.

The housing 102 of the x-ray imaging device 100 may include a cover plate 108. The cover plate 108 may be constructed from a suitable material that is transparent or substantially transparent to x-rays. Suitable materials for the cover plate 108 include carbon fiber, quartz, ceramics, glass, plastics, and metals etc.

The detector 104 may be a digital flat panel detector. The detector 104 may be scintillator-based or a photoconductor-based. The detector 104 may include a large number of detection pixels defining an active detection area 105. The detector 104 may be fixedly attached to the housing 102 or stabilized inside of the housing 102 using other suitable supporting means.

The anti-scatter grid 106 may be disposed above the detector 104 and below the housing cover plate 108. The grid 106 may be attached to the housing 102 via an attachment member 110, which can hold the grid 106 in position as the imaging device 100 is moved in use. By way of example, holes and other suitable features may be provided in the periphery of the grid 106 to allow attachment of the grid 106 with the attachment member 110. The attachment member 110 may be made of any suitable material that is transparent or substantially transparent to x-rays, such as metals e.g. aluminum or plastics.

In some applications, there may be no or minimal moving forces on the imaging device 100 when in use. In such situations, attachment members 110 may not be required and the grid 106 may be free standing, for example, placed on a supporting frame 112 inside the housing 102.

Alternative or in addition to attachment members 110, in some embodiments, a compressible body 114 may be used to support or stabilize the anti-scatter grid 106. For example, in some embodiments, the imaging device 100 may include compression foam 114 configured to hold the detector 104 or components such as a thin reflector integral to the detector glass in place. The compression foam 114 may include a first piece 114a in between the cover plate 108 and the anti-scatter grid 106 and a second piece 114b in between the anti-scatter grid 106 and the detector 104. As such, the anti-scatter grid 106 may be sandwiched between two pieces 114a, 114b of the compression foam 114 and held in place by the compression force transmitted from the housing cover plate 108. The second piece 114b of the compression foam 114 may be thinner than the first piece 114a of the foam such that the grid 106 may be placed close to the detector 104. The first and second pieces of the compression foam 114a, 114b may be two separate pieces. In some embodiments, instead of two separate pieces, a slot may be provided in a single compressible body so that the anti-scatter grid 106 may be received and held in the slot.

The compressible foam 114 may be compressed by a compression force inserted by the device housing cover plate 108. The compression of the compressible foam 114 may transmit a force to the grid 106 and/or detector 104 below the compressible foam 114, thereby holding the grid 106 and/or detector 104 in place.

The anti-scatter grid 106 may be placed as close to the detector 104 as possible. By way of example, the distance between the grid 106 and the detector 104 may range from about 1 to 15 mm, or from about 2 to 10 mm, or about 3 to 5 mm. In some embodiments, the grid 106 may be placed directly on the detector 104.

Exemplary embodiments of an imaging device have been described. Those skilled in the art will appreciate that various modifications may be made within the spirit and scope of the disclosure. All these or other variations and modifications are contemplated by the inventors and within the scope of the disclosure.

The invention claimed is:

1. An x-ray imaging device, comprising:
   a housing comprising a cover plate;
   an x-ray detector placed inside the housing;
   an anti-scatter grid placed inside the housing adjacent to the x-ray detector; and
   a compressible foam between the cover plate and the x-ray detector,
   wherein the compression foam comprises a first piece and a second piece, and the anti-scatter grid is sandwiched between the first and second pieces.

2. The x-ray imaging device of claim 1 wherein the first piece of the compression foam is in between the cover plate of the housing and the anti-scatter grid, and the second piece of the compression foam is in between the anti-scatter grid and the x-ray detector, and the second piece of the compression foam is thinner than the first piece of the foam.

3. The x-ray imaging device of claim 1 wherein the compression foam is provided with a slot forming the first and second pieces and the anti-scatter grid is received and held in the slot.

4. The x-ray imaging device of claim 1 wherein the anti-scatter grid is attached to the housing by an attachment member.

5. The x-ray imaging device of claim 1 wherein the x-ray detector comprises a digital flat panel detector comprising a scintillator layer configured to convert x-ray photons to visible light.

6. The x-ray imaging device of claim 1 wherein the x-ray detector comprises a digital flat panel detector comprising a photoconductor layer configured to convert x-ray photons to electron-hole charges.

7. The x-ray imaging device of claim 1 wherein the anti-scatter grid is distanced from the x-ray detector about 1-15 mm.

8. The x-ray imaging device of claim 7 wherein the anti-scatter grid is distanced from the x-ray detector about 3-5 mm.

* * * * *

UNITED STATES PATENT AND TRADEMARK OFFICE
CERTIFICATE OF CORRECTION

| | |
|---|---|
| PATENT NO. | : 9,620,256 B2 |
| APPLICATION NO. | : 14/474684 |
| DATED | : April 11, 2017 |
| INVENTOR(S) | : Gary Virshup |

It is certified that error appears in the above-identified patent and that said Letters Patent is hereby corrected as shown below:

On the Title Page

Under Assignee, replace "Zug (DE)" with -- Zug (CH) --.

In the Specification

At Column 3 Line 17, replace "CODs" with -- CCDs --.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*